United States Patent [19]

Motzkau

[11] Patent Number: Plant 6,607

[45] Date of Patent: Feb. 14, 1989

[54] AZALEA PLANT NAMED IKON

[75] Inventor: Henry W. Motzkau, Lacey, Wash.

[73] Assignee: Yoder Brothers, Inc., Barberton, Ohio

[21] Appl. No.: 19,360

[22] Filed: Feb. 26, 1987

[51] Int. Cl.[4] ..... A01H 5/00

[52] U.S. Cl. ..... Plt./56

[58] Field of Search ..... Plt./56

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

An Azalea plant named Ikon, particularly characterized by its evergreen foliage, large single hose-in-hose flower form, fuchsia red flower color, compact growth, cold tolerance, ease of budding, and by its excellent shipping and cooler tolerance.

1 Drawing Sheet

The present invention comprises a new and distinct cultivar of Azalea plant named Ikon obtained from crossing certain Azalea selections in a program of controlled hybridization by applicant in Lacey, Wash. The seed parent in the breeding program was identified by Code #2400, and the pollen parent by Code #2515.

The new cultivar is similar in many respects to the cultivar Prize, disclosed in U.S. Plant Pat. No. 3,795, having the same characteristics as Prize of:

1. Evergreen foliage.
2. Fuchsia red flower color.
3. Profusion of bloom.

The new cultivar is distinguished from Prize by the following characteristics:

1. Much less wild growth.
2. Larger, more single type flower.
3. Lighter colored foliage.
4. More cold tolerant.

The new cultivar was selected by applicant in Lacey, Wash. from the seedling progeny of the above mentioned parents. Varietal worth was determined by flowering liners from cuttings taken from the initial selection in both a year round and natural season developmental flowering program over a period of 3½ years. Stock growth was evaluated in the vicinity of Southern Florida.

The new cultivar was first asexually reproduced by applicant in Lacey, Wash. by cuttings, and subsequent propagation has taken place at Fort Myers, Fla. Ikon has been found to retain its distinctive characteristics through successive propagations.

When grown in the vicinity of Fort Myers, Fla., Ikon has a response described as mid-season, and the following detailed description is based on observations made of the new cultivar from field grown plants in Fort Myers, Fla. The response time and blooming period may vary significantly with varying environmental conditions such as temperature and amount of daylight. Suggested flowering period is from January 15 through April 15 in a natural season program and all year round in a controlled program.

The accompanying photograph shows in perspective view the unique features of the new cultivar, with colors being as true as possible with color illustrations of this type.

Color references are to The Royal Horticultural Society Colour Chart. Where a particular color value is not precise, variations from the closest color value have been noted.

Botanical classification: *Rhododendron hybrida*, evergreen type.

Flower:

*Color.*—Reading location and season: All color readings were taken in an office having cool white florescent fixtures and facing a west window. All readings were taken in October between the hours of 10:00 a.m. and 2:00 p.m. in Fort Myers, Fla. General tonality: Darker than fuchsia red 57A-B. Sepals first divide: Much darker than fuchsia red 57A-B. Petals unfurl: Darker than fuchsia red 57A-B. Fully open: Darker than fuchsia red 57A-B. Inside of petals: Darker than fuchsia red 57A-B. Reverse of petals: Darker than fuchsia red 57A-B. Base of petals: Orange pink 38A. Outer hose: Darker than fuchsia red 57A-B. Variations (dotted): Upper 3 petals of each whorl (hose).

*Bud.*—Size: Medium. Form: Conoidal. Opening habit: Cup shaped.

*Bloom.*—Size: Large, average 9.5 cm, range 9–10 cm. Borne: Several together, average 2.5, range 1–3. Form: Single hose-in-hose.

*Blooming habit.*—Once, profusely. Response: Natural season: Mid-season. Year round: All twelve months.

*Calyx.*—Hose.

*Peduncle.*—Length: 3 cm. Aspect: Hairy. Strength: Strong.

*Petals.*—Texture: Soft. Substance: Heavy. Appearance: Inside: Satiny. Outside: Satiny. Form: Round, slightly wavy edge. Arrangement: Imbricate. Fragrance: None. Persistance: Non shatter. Longevity (keeping quality): Greenhouse: 3 weeks. Home: 4 weeks.

Reproductive organs:

*Stamen-anthers.*—5 stamens per flower, normal in appearance. Immature: Reddish pink 52A. Mature: Brownish orange 165A.

*Filaments.*—Columnar, reddish pink 51C.

*Style.*—Columnar, occasionally fasciated. Mature: Reddish purple 53B.

*Stigma.*—Normal, discoid, rarely fasciated. Immature: Yellow green 152B. Mature: Reddish purple 59B.

*Ovaries.*—Normal, hairy.

Fruit: None.

Foliage:

*Type.*—Evergreen.

*Leaflets.*—Single.

*Size.*—Length: Average, 5 cm, range 4.50–5.25 cm. Width: Average, 2.25 cm, range 2.0–2.5 cm. Shape: Oblanceolate. Texture: Dull green, slightly hairy. Rib and mid veins: Slightly depressed. Edge: Entire.

*Color (immature foliage).*—Upper surface: Yellow green 144A. Lower surface: Lighter than green 143C.

*Color (mature foliage).*—Upper surface: Darker than dark green 139A. Lower surface: Darker than light green 138B.

*Petiole.*—Medium length, hairy, light green 143C.

Plant (bush):

*Growth habit.*—Semi-upright.

*Breaking habit.*—Fair.

*Rooting habit.*—Good.

*Budding ease.*—Good.

*Uniformity of budding.*—Good; at times strong shoots are slower to bud.

*Growth regulator.*—Required at some times of the year.

*Stems (color).*—Immature wood: Yellow green 145A. Mature wood: Lighter than brownish orange 165A.

*Responsiveness to day length and temperature.*—Buds easily and uniformly over a wide range of environmental conditions.

*Resistance to cylindrocladium.*—Good.

*Cooler tolerance.*—Excellent.

*Shipping tolerance.*—Excellent.

I claim:

1. A new and distinct cultivar of Azalea named Ikon, as described and illustrated, and characterized particularly as to novelty by its evergreen foliage, fuchsia red flower color, large single hose-in-hose flower form, compact, semi-vigorous growth habit, cold tolerance, ease of budding, and excellent shipping and cooler tolerance.

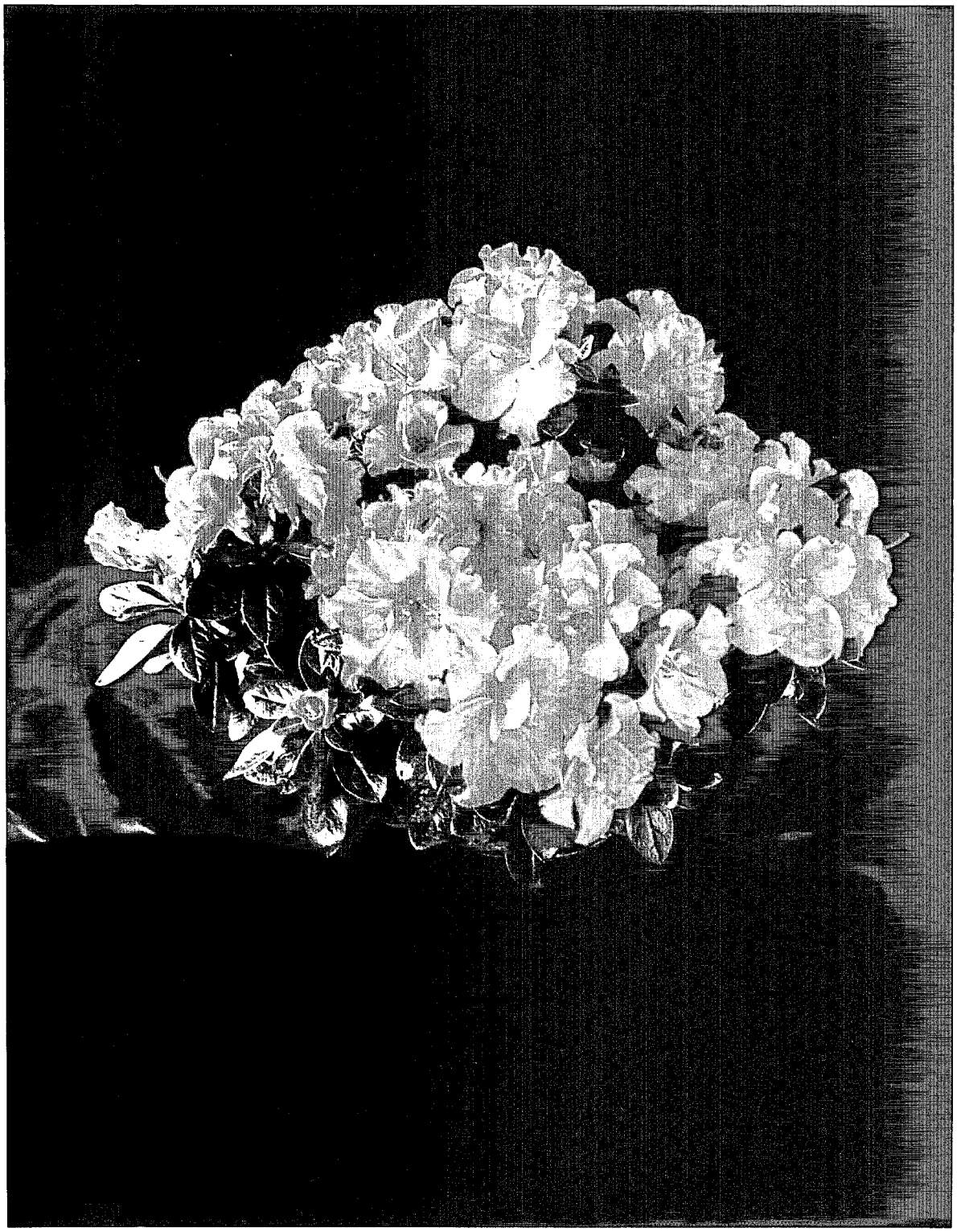

* * * * *